(12) United States Patent
Belkin et al.

(10) Patent No.: US 7,826,509 B2
(45) Date of Patent: Nov. 2, 2010

(54) BROADLY TUNABLE SINGLE-MODE QUANTUM CASCADE LASER SOURCES AND SENSORS

(75) Inventors: Mikhail A. Belkin, Somerville, MA (US); Benjamin G. Lee, Cambridge, MA (US); Ross M. Audet, Palo Alto, CA (US); James B. MacArthur, Somerville, MA (US); Laurent Diehl, Cambridge, MA (US); Christian Pflügl, Cambridge, MA (US); Federico Capasso, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 66 days.

(21) Appl. No.: 11/611,819

(22) Filed: Dec. 15, 2006

(65) Prior Publication Data

US 2008/0144677 A1   Jun. 19, 2008

(51) Int. Cl.
  *H01S 5/00* (2006.01)
  *H01S 3/10* (2006.01)
  *H01S 3/13* (2006.01)

(52) U.S. Cl. ............... 372/50.122; 372/20; 372/29.015; 372/50.121

(58) Field of Classification Search ............... None
See application file for complete search history.

(56) References Cited

U.S. PATENT DOCUMENTS

| | | | | |
|---|---|---|---|---|
| 4,385,386 A | * | 5/1983 | Ozeki et al. | 372/20 |
| 6,104,739 A | * | 8/2000 | Hong et al. | 372/50.11 |
| 6,553,044 B1 | * | 4/2003 | Eden | 372/50.12 |
| 6,560,259 B1 | * | 5/2003 | Hwang | 372/45.01 |
| 2002/0101898 A1 | * | 8/2002 | Lo et al. | 372/46 |
| 2007/0159636 A1 | * | 7/2007 | Jayaraman | 372/50.121 |

* cited by examiner

*Primary Examiner*—Minsun Harvey
*Assistant Examiner*—Sean Hagan
(74) *Attorney, Agent, or Firm*—24IP Law Group; Timothy R. DeWitt

(57) ABSTRACT

A broadly tunable single-mode infrared laser source based on semiconductor lasers. The laser source has two parts: an array of closely-spaced DFB QCLs (or other semiconductor lasers) and a controller that can switch each of the individual lasers in the array on and off, set current for each of the lasers and, and control the temperature of the lasers in the array. The device can be used in portable broadband sensors to simultaneously detect a large number of compounds including chemical and biological agents. A microelectronic controller is combined with an array of individually-addressed DFB QCLs with slightly different DFB grating periods fabricated on the same broadband (or multiple wavelengths) QCL material. This allows building a compact source providing narrow-line broadly-tunable coherent radiation in the Infrared or Terahertz spectral range (as well as in the Ultraviolet and Visible spectral ranges, using semiconductor lasers with different active region design). The performance (tuning range, line width, power level) is comparable to that of external grating tunable semiconductor lasers, but the proposed design is much smaller and much easier to manufacture.

14 Claims, 5 Drawing Sheets

BROADLY TUNABLE SINGLE-MODE QUANTUM CASCADE LASER SOURCES AND SENSORS

CROSS-REFERENCE TO RELATED APPLICATIONS

This work was sponsored by DARPA sub-contract 67F-1080843, under prime contract HR0011-04-1-0032 to California Institute of Technology.

STATEMENT REGARDING FEDERALLY SPONSORED RESEARCH OR DEVELOPMENT

None

BACKGROUND OF THE INVENTION

1. Field of the Invention

The present invention relates to a class of broadly tunable single-mode current-injection semiconductor laser sources 2. Brief Description Of The Related Art Quantum Cascade Lasers (QCLs) are semiconductor lasers that are unipolar and can work in Mid-Infrared and Terahertz spectral regions, which are very important for chemical and biological sensing, remote sensing, high-resolution spectroscopy, infrared detection, countermeasures, and many other applications. In QCLs, optical transitions occur between confined electronic sub-bands of a semiconductor heterostructure. As a result, the emitted photon energy is determined by the thicknesses of the wells and barriers in a heterostructure and can be tailored by band gap engineering. This makes possible fabricating QCLs that emit simultaneously at two or more widely separated wavelengths (this can be done, for example, using heterogeneous active region, consisting of a stack of two or more active regions designed for emission at specific wavelengths, see, for example, a report on QCL emitting at wavelengths 5 and 8 microns by C. Gmachl, D. L. Sivco, J. N. Baillargeon, A. L. Hutchinson, F. Capasso, A. Y. Cho, Applied Physics Letters v. 79, p. 572 (2001)) and fabricating broadband-gain QCLs (this can be done using an active region of "bound-to-continuum" design, see, for example, R. Maulini, M. Beck, J. Faist, E. Gini, Applied Physics Letters v. 84, p. 1659 (2004), using an active region that comprises a stack of two or more active regions based on bound-to-continuum design, each designed for an emission at different wavelengths, see, for example, R. Maulini, A. Mohan, M. Giovannini, J. Faist, E. Gini, Applied Physics Letters v. 88, 201113 (2006), or using heterogeneous active region, consisting of many active regions designed for emission at slightly different wavelengths, see, for example, C. Gmachl, D. L. Sivco, R. Colombelli, F. Capasso, A. Y. Cho, Nature v. 415, p. 883 (2002)). Thus, a single QCL chip can emit light in wide ranges of mid-IR frequencies. We note that, similarly, one can also design QCLs that emit light in the wide range of Terahertz frequencies (see, for example, Benjamin S. Williams, Sushil Kumar, Qing Hu, and John L. Reno, Optics Letters v. 30, p. 2909 (2005)).

Single mode emission is required for most of the applications. To enforce single-mode emission, QCLs are either processed into distributed feedback (DFB) lasers (see, for example, Jerome Faist, Claire Gmachl, Federico Capasso, Carlo Sirtori, Deborah L. Sivco, James N. Baillargeon, and Alfred Y. Cho Applied Physics Letters v. 70, p. 2670 (1997)) or used in external cavity tunable lasers configuration (see, for example, G. P. Luo, C. Peng, H. Q. Le, S. S. Pei, W.-Y. Hwang, B. Ishaug, J. Um, James N. Baillargeon, and C.-H. Lin, Applied Physics Letters v. 78, p. 2834 (2001) and R. Maulini, A. Mohan, M. Giovannini, J. Faist, E. Gini, Applied Physics Letters v. 88, 201113 (2006)). External cavity QCLs have wide tunability but are cumbersome and complex to build as they require well-aligned external optical components and a grating for tuning. DFB lasers are very compact, but DFB QCLs to date have limited tunability, which is achieved either by changing the temperature of the device (see, for example, C. Gmachl, D. L. Sivco, J. N. Baillargeon, A. L. Hutchinson, F. Capasso, A. Y. Cho, Applied Physics Letters v. 79, p. 572 (2001)) or by changing the bias and/or current through the device (see, for example, C. Gmachl, F. Capasso, A. Tredicucci, D. L. Sivco, J. N. Baillargeon, A. L. Hutchinson, and A. Y. Cho, Optics Letters v. 25, p. 230 (2000)).

SUMMARY OF THE INVENTION

The present invention is a new broadly tunable single-mode infrared laser source based on QCLs. The invention comprises two parts: an array of closely-spaced DFB QCLs and a microelectronic controller (which may also incorporate laser driver(s)) that can switch each of the individual lasers in the array on and off, set current for each of the lasers and, and control the temperature of the lasers in the array. The device can be used in portable broadband sensors to simultaneously detect a large number of chemical compounds including chemical and biological agents.

In a preferred embodiment of the present invention, a microelectronic controller (which may also incorporate laser driver(s)) is combined with an array of individually-addressed DFB QCLs. The array of DFB QCLs is fabricated on the same broadband-gain (or multiple wavelengths, or any other) QCL wafer. Each DFB QCL in the array has DFB grating designed to target slightly different emission wavelength. The target emission wavelengths of the DFB QCLs in the array span the full gain bandwidth available in the QCL material. The difference in the target DFB emission wavelengths between two adjacent (in frequency space) DFB QCLs in the array is smaller than the tuning range available with temperature tuning of DFB QCLs. Therefore, by switching between the DFB lasers in the array and using temperature tuning of the individual lasers in the array, one can achieve continuous spectral coverage within the gain bandwidth of an broadband-gain (or multiple wavelengths, or any other) QCL material. This allows building a compact source providing narrow-linewidth broadly-tunable coherent radiation. The performance (tuning range, line width, power level) is comparable to that of external grating tunable QCLs, but embodiments of the present invention are much smaller and much easier to manufacture.

In different embodiments, the present invention may be used with DFB QCLs that work in Infrared or Terahertz spectral range as well as with other semiconductor lasers that operate in Ultraviolet, Visible, Infrared, and Terahertz spectral ranges. In the latter case, the design of the active region of the semiconductor laser can be different from that of QCL. Several details of this invention can be modified in various obvious respects, all without departing from the spirit and scope of the present invention.

In a preferred embodiment, the present invention is a broadly tunable single-mode laser source that comprises an array of closely-spaced semiconductor lasers and a controller. The controller comprises a microelectronic controller and may also include laser driver(s). The controller switches each laser in the array on and off, sets current for each laser and controls a temperature of the lasers in the array. The single-mode laser source may be, for example, an infrared and terahertz laser source. The semiconductor lasers may comprise distributed feedback quantum cascade lasers. Further, each laser in the array may have a slightly different distributed feedback grating. Each distributed feedback grating may be designed for a slightly different target emission wavelength. The lasers in the array may be fabricated on a single broadband-gain or multiple wavelengths or any other wafer of quantum cascade laser material. The emission wavelength of each laser in the array may be tuned by changing a temperature of the laser. The changing of a temperature of the laser may comprise changing a temperature of an active region of the laser.

In a preferred embodiment, each laser in the array has a slightly different target distributed feedback emission wavelength. The difference in the target distributed feedback emission wavelengths between two adjacent (in frequency space) lasers in the array is smaller than the temperature tuning range of an individual distributed feedback laser. Therefore, for any desired wavelength in the wavelength range supported by the gain spectrum of a broadband-gain, or multiple wavelengths, or any other material, a microelectronic controller can select a laser in the array and set its temperature in such a way that that this laser emits at the desired wavelength.

The array of lasers may provide continuous spectral coverage in a spectral range available with a broadband-gain quantum cascade laser material. Further, the array of lasers may provide continuous spectral coverage in a spectral range available within each emission band provided by multiple wavelengths quantum cascade laser material. The array of lasers may provide continuous spectral coverage in a spectral range available within an emission band of any other quantum cascade laser material. The array of lasers together with the microelectronic controller (that may also include laser driver(s)) comprise a broadly tunable single-mode laser source, wherein each laser on a chip can be accessed independently by a compact microelectronic controller (that may also include laser driver(s)). A laser in the array may be wavelength-tuned by changing a bias voltage of the laser. A laser in the array may be wavelength-tuned by heating or cooling of the laser. The lasers in the array may be fabricated with first- or second-order distributed feedback gratings. The lasers in the array provide surface or edge emission.

The lasers in the array may be not only distributed feedback quantum cascade lasers that work in Infrared and Terahertz spectral range, but also other distributed feedback semiconductor lasers that operate in Ultraviolet, Visible, Infrared and Terahertz spectral ranges. In the latter case, the design of the active region of the semiconductor laser can be different from that of quantum cascade laser.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

DESCRIPTION OF THE DRAWINGS

For a more complete understanding of the present invention and the advantages thereof, reference is now made to the following description and the accompanying drawings, in which.

DETAILED DESCRIPTION OF THE PREFERRED EMBODIMENTS

The present invention is a new broadly tunable single-mode infrared laser source based on QCLs. In a preferred embodiment, the invention comprises two parts: an array of closely-spaced DFB QCLs and a microelectronic controller which may incorporate laser driver(s). The controller can switch each of the individual lasers in the array on and off, set the current for each of the individual lasers in the array, and control the temperature of the lasers in the array. The device can be used in portable broadband sensors to simultaneously detect a large number of chemical compounds including chemical and biological agents.

Figure 1:
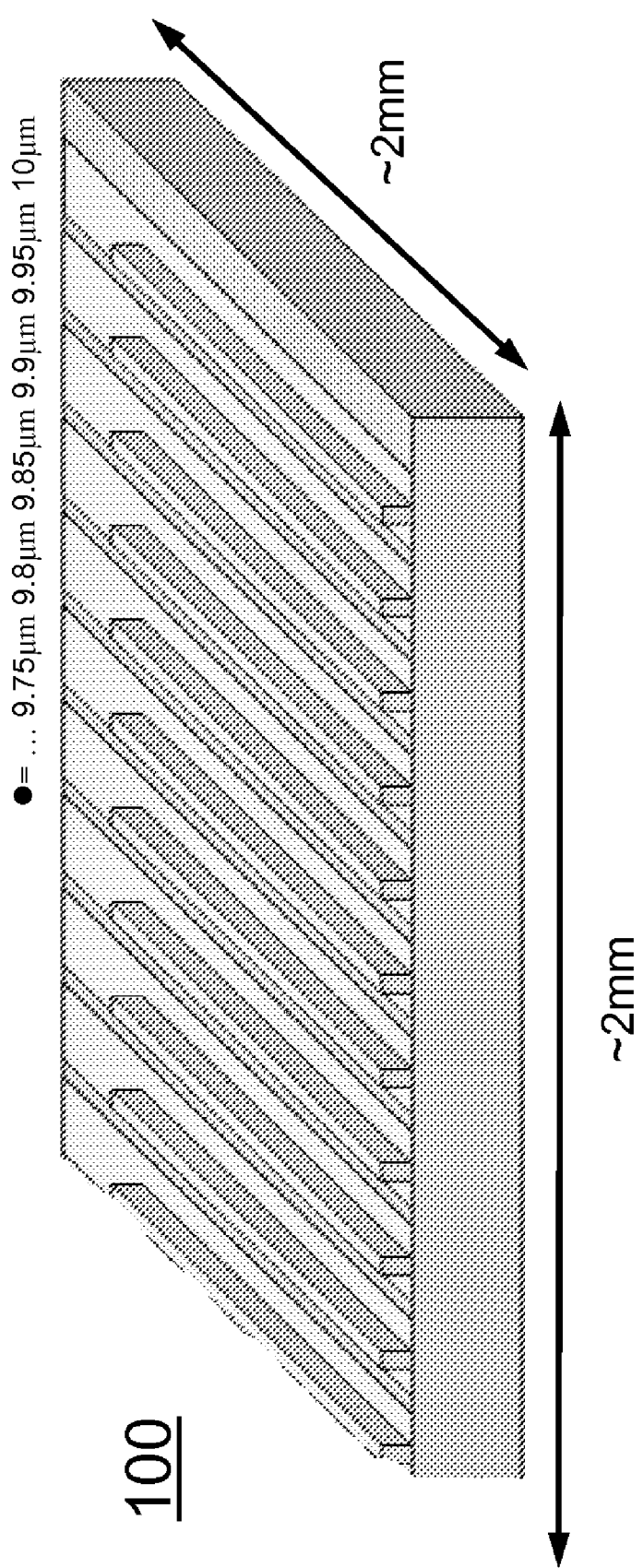
FIG. 1 schematically shows the proposed array of DFB QCLs each with slightly different target emission wavelength.

As shown in FIG. 1, a DFB QCL array 100 is processed on the same broadband-gain (or multiple wavelength, or any other) QCL wafer. Each DFB QCL in the array has slightly different DFB grating. As an example, the target wavelengths (9.75 µm, 9.8 µm, etc.) for each of the DFB QCLs on a chip are listed in FIG. 1 along with the typical dimensions of the chip. Both surface and edge emission designs are possible.

The DFB QCLs are fabricated as close to one another as possible on the same broadband-gain (or multiple wavelength, or any other) wafer of QCL material. Each of these DFB QCLs has a DFB grating designed for a slightly different target emission wavelength. The target DFB wavelengths of the DFB QCLs in the array span the full gain bandwidth available in the QCL material. The real emission wavelength of each DFB QCL on a chip can be tuned (within the range available to DFB QCLs) by changing the temperature of the device or by changing the bias and/or current through the device. The difference in the target DFB emission wavelengths between two adjacent (in frequency space) DFB QCLs in the array is smaller than the temperature tuning range of an individual DFB QCL. Therefore, for any desired wavelength in the wavelength range supported by the gain spectrum of a broadband-gain, or multiple wavelengths, or any other QCL material, one can select a DFB QCL in the array and set its temperature in such a way that that this DFB QCL emits at the desired wavelength. Therefore, as a whole, the array of DFB QCLs can provide continuous spectral coverage in the spectral range available with broadband-gain (or any other) QCL material or within each of the emission bands provided by multiple wavelengths QCL material. Each laser on a chip can be addressed independently by a compact microelectronic controller (which may also incorporate laser driver(s)). The microelectronic controller can switch each of the individual lasers in the array on and off and set current for each of the lasers. It also controls the emission wavelength of each individual DFB QCL by either controlling its temperature or bias voltage and/or current, or by some other means. For example, the temperature tuning of the DFB QCLs in the array can be done by heating or cooling the whole array of lasers at once, or by heating the individual lasers in the DFB array (for example with DC current) and keeping the temperature of the whole array constant. Given typical temperature tuning rate of DFB QCLs of ~0.09 $cm^{-1}$/K (see, for example, C. Gmachl, D. L. Sivco, J. N. Baillargeon, A. L. Hutchinson, F. Capasso, A. Y. Cho, Applied Physics Letters v. 79, p. 572 (2001)), one needs to change the temperature an individual DFB QCL in the array by 35 degrees C. to tune it by 3 $cm^{-1}$.

The DFB QCLs in the array may be fabricated with either first- or second-order DFB gratings (or, in fact, any DFB gratings of any order). With second-order grating, DFB QCLs in the array can provide surface emission (see, for example, Daniel Hofstetter, Jerome Faist, Mattias Beck, and Ursula Oesterle, Applied Physics Letters v. 75, p. 3769 (1999)). For some applications, a broadly tunable single-mode QCL source with an array of surface-emitting DFB QCLs may be more advantageous that that employing traditional edge-emitting QCLs.

Figure 2:
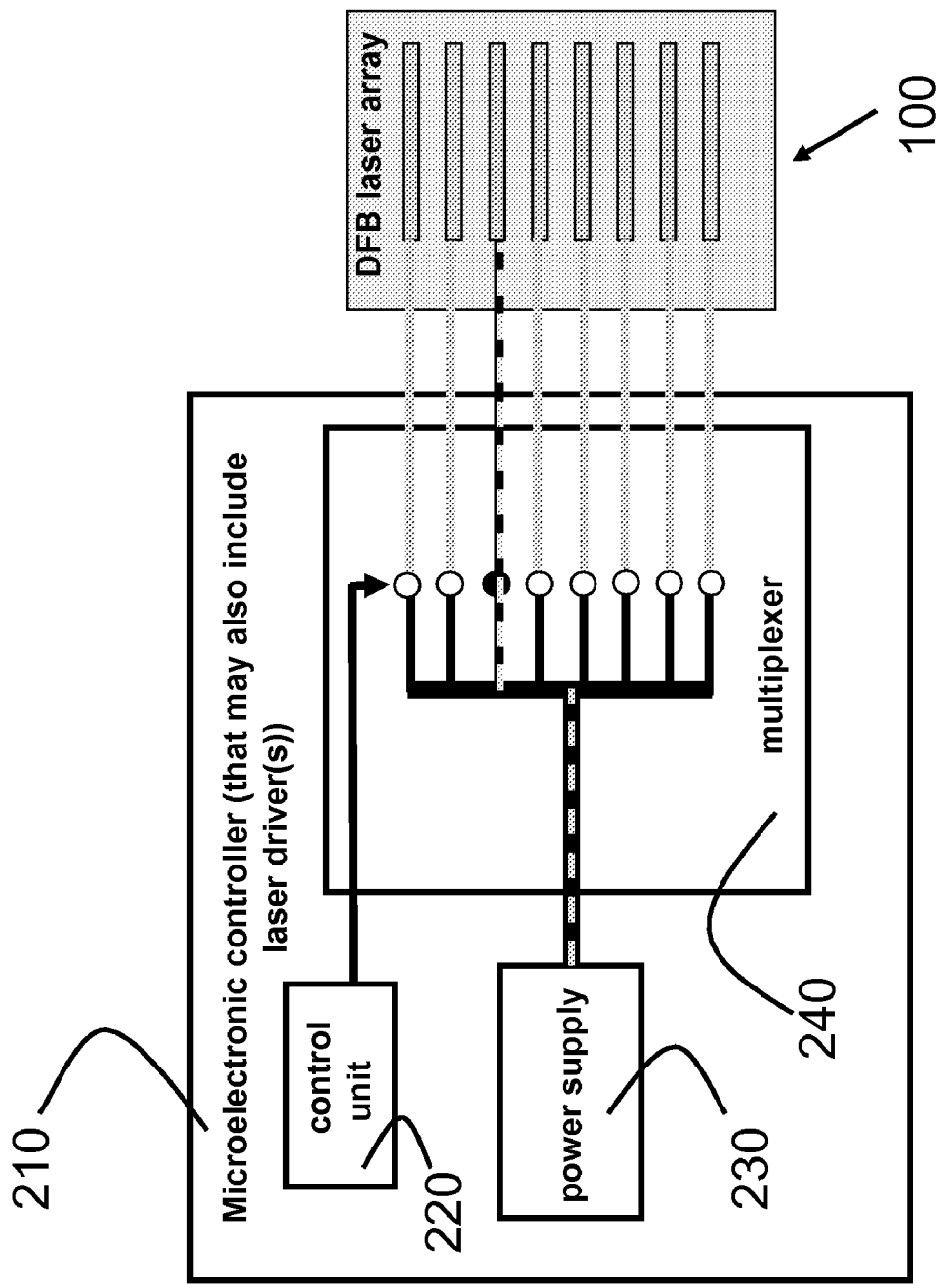
FIG. 2 shows the box diagram of the proposed broadly tunable infrared source, including a microelectronic controller and an array of DFB QCLs.

A schematic diagram of a broadly tunable single-mode coherent infrared source in accordance with a preferred embodiment of the invention is shown in FIG. 2. A controller 210, which may also incorporate laser driver(s), controls multiplexer 230, which receives power from power supply 220.

To give an estimate of the dimensions of the proposed design we note that
- a typical single DFB QCL on a chip is ~1-2 mm long and ~10 µm-wide;
- DFB QCLs can be fabricated on a QCL wafer with spacing 10 µm or less; AND
- each DFB QCL can be temperature tuned by 3 $cm^{-1}$ or more (see, for example, C. Gmachl, D. L. Sivco, J. N. Baillargeon, A. L. Hutchinson, F. Capasso, A. Y. Cho, Applied Physics Letters v. 79, p. 572 (2001) and Claire Gmachl, Federico Capasso, Alessandro Tredicucci, Deborah L. Sivco, James N. Baillargeon, Albert L. Hutchinson, and Alfred Y. Cho, Optics Letters v. 25, p. 230 (2000)).

Therefore, to cover the whole bandwidth of the best (to date) broadband-gain external grating QCL (emission wavelength tunable between 8.2-10.4 microns, see R. Maulini, A. Mohan, M. Giovannini, J. Faist, E. Gini, Applied Physics Letters v. 88, 201113 (2006)) the chip size of the proposed broadly tunable coherent infrared source will be as small as 2×2 mm.

In a preferred embodiment of the invention, a microelectronic controller 210 is combined with an array of individually-addressed DFB QCLs 100 with slightly different DFB grating periods fabricated on the same broadband-gain (or multiple wavelengths, or any other) QCL wafer. This allows building a compact source providing narrow-line broadly-tunable coherent radiation. The performance (tuning range, line width, power level) of the proposed device is comparable to that of external grating tunable QCLs, but the proposed design is much smaller and much easier to manufacture.

This invention has wide ranging applications in all areas where a compact widely tunable narrow-linewidth light source is desired, including chemical and biological sensing, remote sensing, high-resolution spectroscopy, infrared detection, pollution monitoring, combustion diagnostics, and many other applications. The compactness of the proposed device makes possible to integrate it with a microfluidic delivery system and build a millimeter-sized infrared microfluidic spectrometer for lab-on-a-chip applications. Examples of devices based on this invention will be discussed.

The present invention can be used with DFB QCLs that work in Infrared and Terahertz spectral range as well as with other semiconductor lasers that operate in Ultraviolet, Visible, Infrared and Terahertz spectral ranges. In the latter case, the design of the active region of the semiconductor laser can be different from that of quantum cascade laser. Several details of this invention can be modified in various obvious respects, all without departing from the spirit and scope of the present invention.

The broadly tunable single-mode quantum cascade laser source of the present invention offers a number of advantages over the external grating broadly tunable QCL.

(1). Fewer Components.

The broadly tunable single-mode quantum cascade laser source of the present invention does not require any external optics or any moving parts for tuning. The array of DFB QCLs is microfabricated on a single QCL material wafer and the microelectronic controller, which may also incorporate laser driver(s), contains only electronic components. As a result, our design is much simpler than external grating design which requires external optical components and moving grating. The packaging cost is much lower, as there is no need for careful alignment of the lasers and optics.

(2). Smaller Footprint

The present invention is intrinsically small in size. The dimensions of the DFB laser array can be as small as 2×2 mm (see estimates above). External grating broadly tunable QCLs cannot be easily made small as they require a moving grating and external optical components. Both our design and external grating broadly tunable QCLs require microelectronic controller to select the emission wavelength.

(3). Better Temperature Performance and Higher Power Output

Our design of the broadly tunable QCL source may offer better temperature performance and higher output powers that external grating broadly tunable QCL. This is because external grating tunable QCL requires light to be coupled out of a QCL cavity, then projected to a diffraction grating that provides wavelength selection, and then re-injected back into a QCL. All these steps induce laser radiation losses. In our design, the wavelength selection is done inside the QCL itself through a built-in DFB grating. Thus it avoids the losses intrinsic to external cavity QCLs.

Examples of Instruments Based on Proposed Broadly Tunable QCL Source

1. Microfluidic Spectrometer

Figure 3:
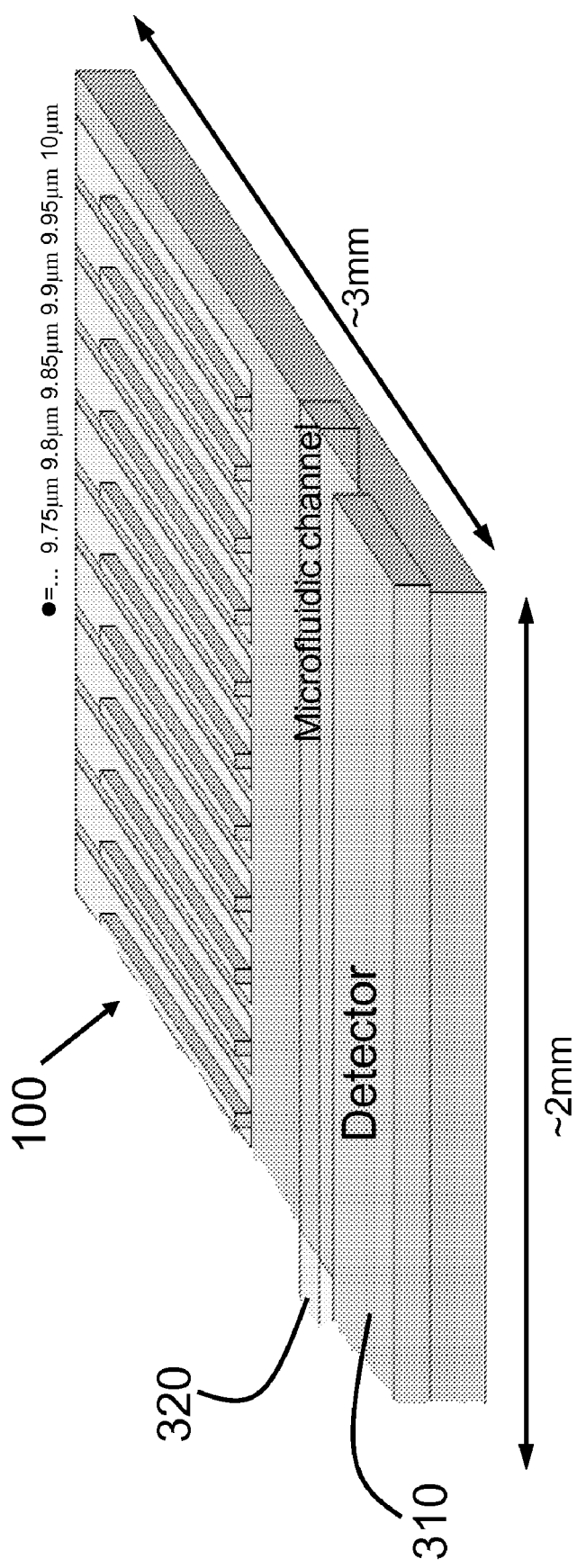
FIG. 3 is a schematics diagram of a microfluidic infrared spectrometer based on the proposed broadly tunable infrared source integrated with a microfluidic delivery system and a detector.

The proposed broadly tunable single-mode QCL source 100 can be integrated with a microfluidic delivery system 320 and a detector 310 to make a millimeter-sized microfluidic infrared spectrometer as shown in FIG. 3. This spectrometer can be used as a stand-alone unit, or it can be integrated within a lab-on-a-chip.

2. Photoacoustic Spectroscopy of Gases

Figure 4:
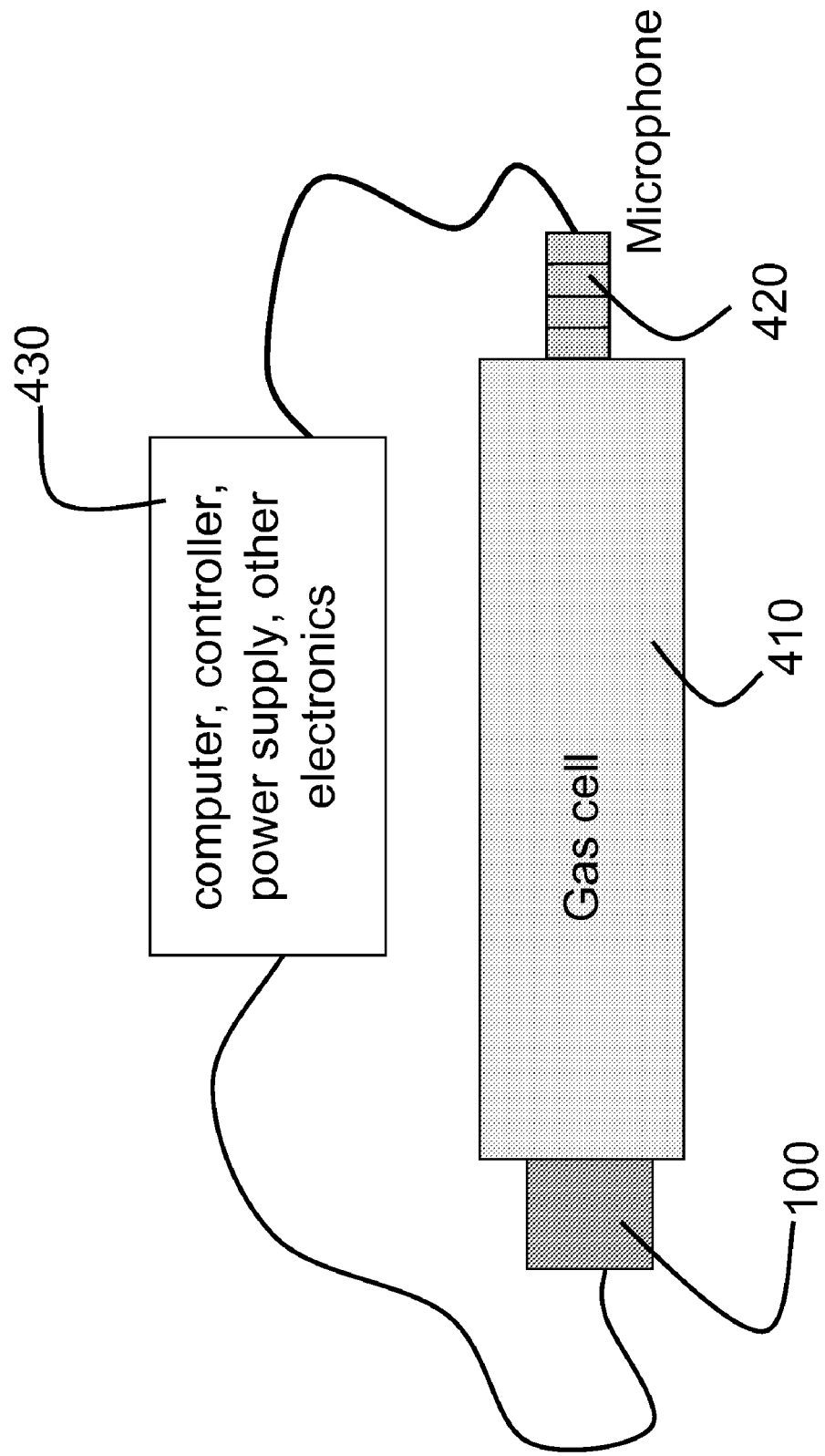
FIG. 4 is a schematic diagram of a photoacoustic gas detector, suitable for simultaneous detection of several different gases, based on proposed broadly tunable single-mode infrared source.

The proposed broadly tunable single-mode QCL source 100 can be integrated into the setup used in photoacoustic spectroscopy as shown in FIG. 4. The setup has a gas cell 410, a microphone 420, and a computer, along with other electronics, 430. It has already been demonstrated that with a single DFB QCL, one can successfully build extremely sensitive gas sensors based on the principle of photoacoustic spectroscopy (see, for example, Stefano Barbieri, Jean-Paul Pellaux, Eric Studemann, and Daniel Rosset, Review of Scientific Instruments v. 73, p. 2458 (2002)). Integration of a broadly tunable single-mode QCL source in accordance with the present invention will make these sensors capable of detecting a number of different gases simultaneously.

3. Absorption Spectroscopy of Gases

Figure 5:
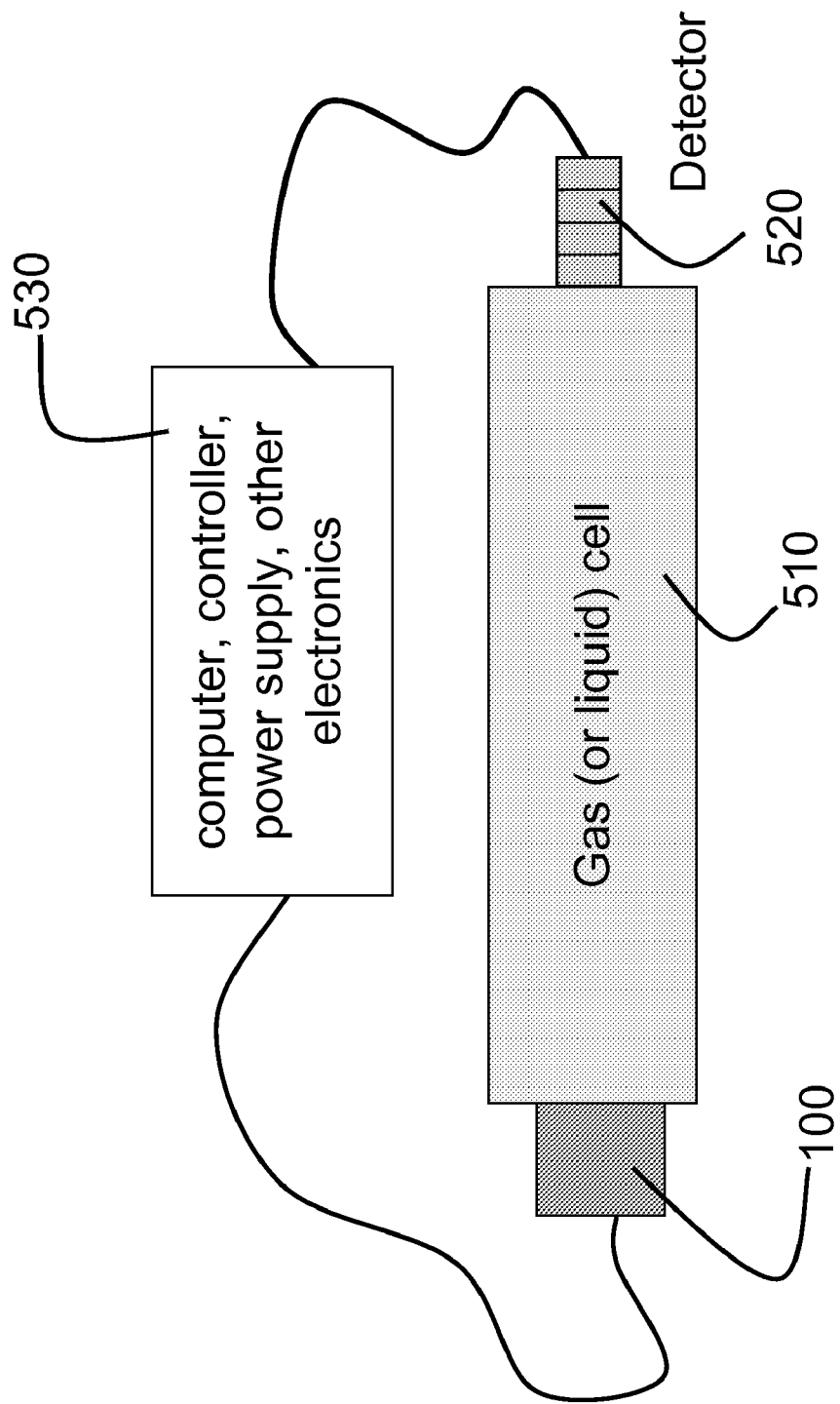
FIG. 5 is a schematic diagram of an absorption spectroscopy gas detector based on proposed broadly tunable single-mode infrared source, suitable for simultaneous detection of several different gases.

The proposed broadly tunable single-mode QCL source 100 can be integrated into the setup used in absorption spectroscopy as shown in FIG. 5. The setup has a gas (or liquid) cell 510, a light detector 520, and a computer, along with other electronics, 530. It has already been demonstrated that with a single DFB QCL, one can successfully build extremely sensitive gas sensors based on the principle of absorption spectroscopy (see, for example, M. R. McCurdy, Y. A. Bakhirkin, F. K. Tittel, Applied Physics B v. 85, p. 445 (2006)). Integration of a broadly tunable single-mode QCL source in accordance with the present invention will make these sensors capable of detecting a number of different gases or liquids simultaneously.

4. Remote Sensing

The proposed broadly tunable single-mode QCL source 100 can be integrated into the setup used for remote sensing application, including remote detection of explosives. Integration of a broadly tunable single-mode QCL source in accordance with the present invention will make these remote sensors capable of detecting a number of different compounds simultaneously.

5. Other Applications

In general, the proposed broadly tunable single-mode QCL source can be used in any application that requires a high-power narrow-linewidth broadly tunable source in Infrared or Terahertz spectral ranges.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

The invention claimed is:

1. A continuously tunable single-mode quantum cascade laser source comprising:

an array of individually addressed closely-spaced mid-infrared or THz quantum cascade lasers fabricated on the same laser wafer, wherein each laser in said array has a slightly different emission wavelength and that a difference in the emission wavelengths, set by the distributed feedback grating, between two lasers in the array that are adjacent in frequency space, is sufficiently small such that for any desired wavelength in a wavelength range supported by a broadband-gain, or multiple wavelengths, or any other quantum cascade laser material, said controller may set the temperature of a laser in the array in such a way that said laser emits at the desired wavelength and a difference in the target emission wavelengths between two adjacent lasers in the array is smaller than a tuning range available with temperature tuning of each of said lasers, and wherein each laser on a chip can be addressed independently by a compact microelectronic controller; and a compact microelectronic controller, wherein said controller switches each laser in the array on and off, sets current for each said laser, controls and sets a temperature of each individual laser in said array as well as the temperature of the array as a whole to produce a continuously tunable single-mode quantum cascade laser source.

2. A continuously tunable single-mode quantum cascade laser source according to claim 1, wherein said single-mode quantum cascade laser source is one of a mid-infrared and terahertz quantum cascade laser source.

3. A continuously tunable single-mode quantum cascade laser source according to claim 1, wherein said quantum cascade lasers comprise distributed feedback quantum cascade lasers.

4. A continuously tunable single-mode quantum cascade laser source according to claim 1, wherein said lasers in said array are fabricated on a single broadband-gain or multiple wavelengths quantum cascade laser material.

5. A continuously tunable single-mode quantum cascade laser source according to claim 1, wherein a laser in said array may be tuned by changing the temperature of said laser.

6. A continuously tunable single-mode quantum cascade laser source according to claim 5, wherein said changing of the temperature of said laser comprises changing the temperature of an active region of said laser.

7. A continuously tunable single-mode quantum cascade laser source according to claim 1, wherein said array of lasers provides continuous spectral coverage in a spectral range available within each emission band provided by multiple wavelengths quantum cascade laser material.

8. A continuously tunable single-mode quantum cascade laser source according to claim 1, wherein said controller comprises a microelectronic controller.

9. A continuously tunable single-mode quantum cascade laser source according to claim 1, wherein a laser in said array may be wavelength-tuned by changing a bias voltage of said laser.

10. A continuously tunable single-mode quantum cascade laser source according to claim 1, wherein a laser in said array may be wavelength-tuned by heating or cooling of said laser.

11. A continuously tunable single-mode quantum cascade laser source according to claim 1, wherein said lasers in said array are fabricated with first- or second-order distributed feedback gratings.

12. A continuously tunable single-mode quantum cascade laser source according to claim 1, wherein said lasers in said array provide surface emission.

13. A continuously tunable single-mode quantum cascade laser source according to claim 1, wherein said lasers in said array provide edge emission.

14. A continuously tunable single-mode quantum cascade laser source according to claim 1, wherein said controller switches at least two lasers in said array simultaneously.

* * * * *